United States Patent [19]
Hoshino et al.

[11] Patent Number: 5,747,301
[45] Date of Patent: May 5, 1998

[54] D-SORBITOL DEHYDROGENASE

[75] Inventors: Tatsuo Hoshino, Kamakura; Setsuko Ojima, Fujisawa; Teruhide Sugisawa, Yokohama, all of Japan

[73] Assignee: Roche Vitamins Inc., Parsippany, N.J.

[21] Appl. No.: 606,807

[22] Filed: Feb. 26, 1996

[30] Foreign Application Priority Data

Feb. 27, 1995 [EP]  European Pat. Off. .............. 95102748

[51] Int. Cl.$^6$ .............................. C12P 19/02; C12N 9/02; C12N 9/04; C12N 1/00
[52] U.S. Cl. ........................ 435/105; 435/189; 435/190; 435/823
[58] Field of Search ................... 435/105, 190, 435/189, 823

[56] References Cited

PUBLICATIONS

Baker et al, FEMS Microbiology Letters 18:123–125 (1983).
Kersters et al, Methods in Enzymology 9:170–179, Wood, ed. (1966).
J.T. Cummins, et al., J. Biol. Chem. vol. 224, pp. 323–329 (1957).
T. Sugisawa, et al., Argic. Biol. Chem. vol. 55, pp. 2043–2049 (1991).
E. Shinagawa, et al., Argic. Biol. Chem. vol. 46, pp. 135–141 (1982).

*Primary Examiner*—Leon B. Lankford, Jr.
*Assistant Examiner*—Francisco C. Prats
*Attorney, Agent, or Firm*—George W. Johnston; Dennis P. Tramaloni; Bruce A. Pokras

[57] ABSTRACT

A D-sorbitol dehydrogenase in homogenous form, which catalyzes the oxidation of D-sorbitol to L-sorbose, has a molecular structure consisting of homologous subunits of molecular weight 79,000±5,000 each, a substrate specificity for polyols and an optimum pH of 6.0–7.0. Said D-sorbitol dehydrogenase is producible by a process comprising cultivating a microorganism belonging to the genus Gluconobacter or Acetobacter, or a mutant or variant thereof, which is capable of producing the D-sorbitol dehydrogenase in the cells and isolating it from the cells, e.g. by disrupting the cells and isolation from cell-free extract of the disrupted cells. The so-isolated D-sorbitol dehydrogenase is useful for catalyzing the oxidation of D-sorbitol to L-sorbose, the latter being an important intermediate for the production of vitamin C.

11 Claims, No Drawings

D-SORBITOL DEHYDROGENASE

BACKGROUND OF THE INVENTION

Enzymes which catalyze the oxidation of D-sorbitol to L-sorbose are known. J. T. Cummins, T. E. King and V. H. Cheldelin (*J. Biol. Chem.*, 224,323–329, 1957) reported that the cell free extract of *Acetobacter suboxydans* (syn. *Gluconobacter suboxydans*) contains three enzymes participating in pathways of D-sorbitol oxidation. Two of these enzymes catalyzing the oxidation of D-sorbitol to L-sorbose have been purified. One was isolated as nicotine amide adenine dinucleotide phosphate (hereinafter referred to as NADP)-dependent L-sorbose reductase from the soluble fraction of *Gluconobacter melanogenus* IFO 3293 by T. Sugisawa, T. Hoshino and A. Fujiwara (*Agric. Biol. Chem.*, 55,2043–2049, 1991), and another was isolated as membrane-bound D-sorbitol dehydrogenase from *Gluconobacter suboxydans* var. α IFO 3254 by E. Shinagawa, K. Matsushita, O. Adachi and M. Ameyama (*Agric. Biol. Chem.*, 46, 135–141, 1982).

SUMMARY OF THE INVENTION

The present invention concerns a novel D-sorbitol dehydrogenase, a process for producing the same and a process for producing ketoses, especially L-sorbose utilizing said enzyme.

The novel D-sorbitol dehydrogenase (hereinafter referred to as SLDH) provided by the present invention catalyzes the oxidation of D-sorbitol to L-sorbose. L-Sorbose is an important intermediate for the production of vitamin C.

DETAILED DESCRIPTION OF THE INVENTION

The SLDH provided by the present invention is clearly distinct from the enzymes of Cummins et al. and Shinagawa et al. in the subunit structure of the enzyme, the molecular weight, substrate specificity and optimum pH. The molecular weight of the NADP-dependent L-sorbose reductase of Sugisawa et al. is 60,000. The membrane-bound D-sorbitol dehydrogenase isolated by E. Shinagawa et al. consisted of three kinds of subunits with molecular weights of 63,000, 51,000 and 17,000. This enzyme oxidized D-sorbitol specifically, and also oxidized D-mannitol at 5% of the reaction rate with D-sorbitol. However, the Shinagawa et al. enzyme did not oxidize D-arabitol or erythritol. Furthermore, Shinagawa et al. showed that the optimum pH of the enzyme was 4.5, and that the enzyme activity was stable at pH 5.0. However, 92% of the activity was lost at pH 7.0.

In distinction from the enzymes of Sugisawa et al. and Shinagawa et al., the molecular weight of the SLDH provided by the present invention is about 800,000±50,000 and it consists of ten homologous subunits having a molecular weight of 79,000±5,000, each. Further, the SLDH of the present invention does not require NADP to catalyze the reaction. Moreover, the SLDH of the present invention oxidizes not only D-sorbitol and D-mannitol, but also D-arabitol and erythritol. The optimum pH of the SLDH of the present invention is 6.0, and its activity is stable even at pH 8.0.

The microorganisms used for the present invention are microorganisms belonging to genus Gluconobacter and Acetobacter. Mutants and variants of said microorganism can be also used in the present invention. Thus, the present invention comprises an SLDH enzyme in homogenous form from microorganisms of the genus Gluconobacter and Acetobacter which acts on D-sorbitol to produce L-sorbose (i.e., catalyzes the oxidation of D-sorbitol to L-sorbose), and which has the following physico-chemical properties:

a) Molecular structure: A molecular weight of 800,000±50,000 consisting of ten homologous subunits having a molecular weight of 79,000±5,000;

b) Substrate specificity: Active on polyols;

c) Optimum pH for oxidizing D-sorbitol to L-sorbose: 6.0–7.0;

d) Oxidizes D-sorbitol to L-sorbose at a pH in the range from pH 5.5–8.0.

Preferred microorganisms of the genus Gluconobacter and Acetobacter are described herein. The most preferred microorganism, *Gluconobacter suboxydans* IFO 3255, has been deposited at the Deutsche Sammlung von Mikroorganismen und Zellkulturen GmbH (DSM), Mascheroder Weg 1b, D-38124 Braunschweig, Germany on Feb. 13, 1995 under the Budapest Treaty. The allotted deposit number is DSM 9715.

The invention also comprises a method for producing L-sorbose from D-sorbitol which comprises reacting the D-sorbitol in an aqueous medium under aerobic conditions in the presence of a catalytically effective amount of the SLDH of the present invention and an effective amount of an electron acceptor whereby the D-sorbitol is oxidized to the L-sorbose. Any conventional compound which has the ability to act as an electron acceptor can be utilized in conjunction with the enzyme of this invention. As an electron acceptor, 2,6-dichlorophenolindophenol (hereinafter referred to as DCIP), phenazine methosulfate (hereinafter referred to as PMS), ferricyanide or cytochrome c are preferred.

The process of the invention may be carried out under any conventional conditions whereby the SLDH of the invention oxidizes D-sorbitol to L-sorbose. The reaction is preferably carried out at a pH in the range from about 5.5 to about 8.0 and at a temperature in the range from about 20° to about 50° C. More preferably, the process of the invention is carried out at a pH in the range from about 6.0 to 7.0 and at a temperature in the range from about 20° to 40° C.

It is another object of the present invention to provide a process for producing the novel enzyme SLDH by cultivation of a microorganism belonging to the genus Gluconobacter or Acetobacter, or a mutant thereof, which is capable of producing the SLDH in the cells, disruption of the cells, isolation and purification of the enzyme from cell-free extract of disrupted cells, preferably from the membrane fraction of the microorganism. A still further object of the present invention is to provide a process for producing L-sorbose utilizing said enzyme, SLDH.

The further physico-chemical properties of the purified sample of the novel SLDH prepared according to the Examples herein after are as follows:

1) Enzyme activity

The novel SLDH of the present invention catalyzes the oxidation of D-sorbitol to L-sorbose in the presence of an electron acceptor according to the following reaction formula:

D-Sorbitol+Electron acceptor→L-Sorbose+Reduced electron acceptor

The enzyme does not utilize oxygen as an electron acceptor. This was affirmed by the lack of catalytic activity of the enzyme in an attempt to convert D-sorbitol to L-sorbose using oxygen as a possible electron acceptor.

Furthermore, no oxygen consumption was detected in the reaction mixture as detected by a dissolved oxygen probe. However, any conventional compound which has the ability to act as an electron acceptor can be utilized in conjunction with the enzyme of this invention. As an electron acceptor, 2,6-dichlorophenolindophenol (hereinafter referred to as DCIP), phenazine methosulfate (hereinafter referred to as PMS), ferricyanide or cytochrome c are preferred.

The enzyme assay was performed as follows. The basal reaction mixture for assaying D-sorbitol dehydrogenase activity consisted of 50 mM potassium phosphate buffer (pH 6.0), 0.25 mM DCIP and 0.325 mM PMS, which was prepared just before the assay. A cuvette with a 1-cm light path contained 0.4 ml of the basal reaction mixture, 0.1 ml of 0.4M D-sorbitol and enzyme solution with a total volume of 0.51 ml. The reference cuvette contained all components except for the substrate. The reaction was started at 25° C. with D-sorbitol and the enzyme activity was measured as the initial reduction rate of DCIP at 600 nm. One enzyme unit is defined as the amount of the enzyme that catalyzes the reduction of 1 μmol of DCIP per minute. The extinction coefficient of DCIP at pH 6.0 was 10.8 $mM^{-1}$.

2) Substrate specificity

Substrate specificity of the enzyme was determined using the same enzyme assay method as described above in 1) except that various substrate solutions (100 mM) were used instead of D-sorbitol. The results of the measurement are shown in Table 1. Among the tested substances, D-sorbitol, D-arabitol, erythritol and glycerol were highly oxidized, and D-mannitol and D-adonitol were also oxidized, at 49.9 and 66.6% of the reaction rate of D-sorbitol.

TABLE 1

Substrate specificity of the purified D-sorbitol dehydrogenase

| Substrate | Relative activity[a] (%) |
|---|---|
| D-Sorbitol | 100 |
| D-Mannitol | 49.9 |
| D-Arabitol | 175 |
| meso-Erythritol | 172 |
| D-Adonitol | 66.6 |
| Glycerol | 117 |
| D-Glucose | 0 |
| D-Fructose | 0 |
| L-Sorbose | 0 |
| D-Xylitol | 0 |
| Methanol | 0 |
| Ethanol | 0 |
| Sucrose | 0 |

[a]Relative activity is expressed as the percent of the reaction rate obtained with the substrate D-sorbitol.

3) Optimum pH

The correlation between the reaction rate of the SLDH and pH was determined using the same enzyme assay method as described above in 1) except that various pH's and buffers were used. The results are shown in Table 2. The enzyme showed optimum pH values of 6.0–7.0 and showed the highest activity at pH 6.0.

TABLE 2

Optimum pH for the SLDH activity

| | Relative activity (%)[a] Buffers (0.1M) | | |
|---|---|---|---|
| pH value | McIlvain | Potassium phosphate | Tris-HCl |
| 4.0 | — | — | — |
| 4.5 | — | — | — |
| 5.0 | — | — | — |
| 5.5 | 22.2 | — | — |
| 6.0 | 82.2 | 100.0 | — |
| 6.5 | 48.9 | 73.3 | — |
| 7.0 | 40.0 | 57.8 | 60.0 |
| 7.5 | 33.3 | 51.1 | 31.1 |
| 8.0 | 31.1 | — | 11.1 |
| 8.5 | — | — | 0 |
| 9.0 | — | — | 0 |

[a]Data are expressed as a percentage of the activity at pH 6.0 of potassium phosphate buffer.

4) pH stability

The enzyme was kept standing in buffers of various pHs for 16 hours at 4° C., and then the residual activity was measured using the same enzyme assay method as described above in 1). The results of the measurement are shown in Table 3. Over 60% of the activity remained at pHs between 7.0 and 9.0.

TABLE 3 pH Stability for the SLDH activity

| | Relative activity (%)[a] Buffers (0.1M) | | |
|---|---|---|---|
| pH value | McIlvain | Potassium phosphate | Tris-HCl |
| 4.0 | — | — | — |
| 4.5 | 0 | — | — |
| 5.0 | 0 | — | — |
| 5.5 | 0 | — | — |
| 6.0 | 0 | 0 | — |
| 6.5 | 0 | 10.0 | — |
| 7.0 | 50.0 | 60.0 | 75.0 |
| 7.5 | 60.0 | 70.0 | 80.0 |
| 8.0 | 100.0 | — | 80.0 |
| 8.5 | — | — | 95.0 |
| 9.0 | — | — | 85.0 |

[a]Data are expressed as a percentage of the activity at pH 8.0 of McIlvain buffer.

5) Thermostability

Thermostability was tested by incubating the enzyme for 5 minutes at various temperatures in 0.01M potassium phosphate buffer (pH 7.0). The residual activity was measured using the same enzyme assay method as described above in 1), after which the treated enzyme was cooled immediately in ice water. The results are shown in Table 4. The enzyme was stable up to 35° C., and lost about 20, 70 and 90% of its activity after it had been incubated at 40°, 50° and 60° C., respectively.

TABLE 4

Temperature stability for the SLDH activity

| Temperature (°C.) | Relative activity[a] (%) |
|---|---|
| 0 | 100 |
| 20 | 100 |
| 25 | 106 |
| 30 | 106 |
| 35 | 106 |
| 40 | 82.4 |
| 50 | 29.4 |
| 60 | 11.8 |

[a] Data are expressed as a percentage of the activity at 20° C.

6) Optimum temperature

The enzyme activities were measured at temperatures from 20° to 60° C. in the same assay method as described above in 1). The results are shown in Table 5. The enzyme showed optimum temperature at from 20° to 40° C. and showed the highest activity at 30° C. The decrease of 60 and 70% in its activity was observed at 45° and 50° C., respectively, and no more activity was detected at 60° C.

TABLE 5

Optimum temperature for the SLDH activity

| Temperature (°C.) | Relative activity[a] (%) |
|---|---|
| 20 | 82.1 |
| 28 | 83.2 |
| 30 | 100 |
| 35 | 91.7 |
| 37 | 77.0 |
| 40 | 74.8 |
| 45 | 39.9 |
| 50 | 28.9 |
| 55 | 4.5 |
| 60 | 0 |

[a] Data are expressed as a percentage of the activity at 30° C.

7) Effects of metal ions and inhibitors

The effects of metal ions and inhibitors on the SLDH activity were examined by measuring the activity using the same assay method as described above in 1). After the addition of enzyme solution to the basal reaction mixture each metal solution was stirred in and the reaction was started with the addition of D-sorbitol. As shown in Table 6, 8 to 17% of the activity was stimulated by the addition of 0.91 and 1.79 mM $Co^{2+}$. However, the addition of 0.91 mM $Cu^{2+}$ and $Fe^{3+}$ in each case was strongly inhibitory, and the addition of $Zn^{2+}$ was inhibitory by 44 to 68%. The effects of various inhibitors on the activity were investigated. As shown in Table 7, quinine hydrochloride and monoiodoacetate were inhibitory by 25% and 75%, respectively.

TABLE 6

Effects of various metals on the activity of D-sorbitol dehydrogenase

| Metal | Relative activity (%) Concentration (mM) | |
|---|---|---|
| | 0.91 | 1.79 |
| $Ca(NO_3)_2.4H_2O$ | 96 | 96 |
| $CaCl_2$ | 96 | 96 |
| $CoCl_2.6H_2O$ | 117 | 108 |
| $CuSO_4$ | 0 | 0 |

TABLE 6-continued

Effects of various metals on the activity of D-sorbitol dehydrogenase

| Metal | Relative activity (%) Concentration (mM) | |
|---|---|---|
| | 0.91 | 1.79 |
| $Cu(NO_3)_2.3H_2O$ | 0 | 0 |
| $CuCl_2.2H_2O$ | 0 | 0 |
| $Fe_2(SO_4)_3.xH_2O$ | 0 | 0 |
| $MgCl_2.6H_2O$ | 88 | 92 |
| $MnCl_2.4H_2O$ | 80 | 88 |
| $MnSO_4.4-6H_2O$ | 88 | 88 |
| $Na_2MoO_4.2H_2O$ | 68 | 96 |
| $TiCl_4$ | 96 | 88 |
| $ZnCl_2$ | 56 | 32 |
| $ZnSO_4.7H_2O$ | 44 | 40 |
| $NiSO_4.6H_2O$ | 88 | 108 |

Relative activity is expressed as the percentage of the reaction rate obtained without metal compounds shown in the table.

TABLE 7

Effects of inhibitors on the activity of D-sorbitol dehydrogenase

| Metal | Relative activity (%) Concentration (mM) | |
|---|---|---|
| | 0.96 | 1.89 |
| EDTA | 96.7 | 100 |
| Quinine-HCl | 79.2 | 75.0 |
| N-Ethylmaleimide | 116.7 | 100 |
| $NaN_3$ | 91.7 | 112.5 |
| Monoiodoacetate | 75.0 | 25.0 |
| Sodium fluoroacetate | 104.2 | 108.3 |
| Sodium fluoride | 100 | 100 |
| $Na_2HAsO_4.7H_2O$ | 116.7 | 120.0 |

Relative activity is expressed as the percentage of the reaction rate obtained without any inhibitors shown in the table.

8) Effects of substrate concentration on reaction rate

The velocity of the oxidizing reaction on varying the concentration of D-sorbitol from 0.5 to 80 mM was measured to determine the Km value for D-sorbitol. The apparent Michaelis constant was calculated to be 18 mM with DCIP as an electron acceptor for the reaction.

9) Molecular weight

The molecular weight of the native SLDH was determined by HPLC using a size exclusion gel column at 280 nm and a flow rate of 1.0 ml per minute. The purified SLDH consisted of an homologous subunit with a molecular weight of 79,000±5,000 in the presence of sodium dodecyl sulfate (SDS).

10) Purification procedure

Purification of the SLDH is effected by the combination of known purification methods such as ion exchange chromatography, liquid chromatography, adsorption chromatography, gel-filtration chromatography, gel-electrophoresis, salting out and dialysis.

The SLDH provided by the present invention can be prepared by cultivating an appropriate microorganism, disrupting the cells and isolating and purifying it from cell free extract of disrupted cells, preferably from the membrane fraction of the microorganism.

Examples of the strains most preferably used in the present invention are *Gluconobacter albidus* IFO 3250, *Gluconobacter albidus* IFO 3251, *Gluconobacter albidus*

IFO 3253, *Gluconobacter capsulatus* IFO 3462, *Gluconobacter cerinus* IFO 3263, *Gluconobacter cerinus* IFO 3264, *Gluconobacter cerinus* IFO 3265, *Gluconobacter cerinus* IFO 3267, *Gluconobacter cerinus* IFO 3270, *Gluconobacter dioxyacetonicus* IFO 3271, *Gluconobacter dioxyacetonicus* IFO 3274, *Gluconobacter gluconicus* IFO 3171, *Gluconobacter gluconicus* IFO 3285, *Gluconobacter gluconicus* IFO 3286, *Gluconobacter industrius* IFO 3260, *Gluconobacter melanogenus* IFO 3292, *Gluconobacter melanogenus* IFO 3293, *Gluconobacter melanogenus* IFO 3294, *Gluconobacter nonoxygluconicus* IFO 3276, *Gluconobacter oxydans* IFO 3189, *Gluconobacter oxydans subsp. sphaericus* IFO 12467, *Gluconobacter roseus* IFO 3990, *Gluconobacter rubiginosus* IFO 3244, *Gluconobacter suboxydans* IFO 3130, *Gluconobacter suboxydans* IFO 3172, *Gluconobacter suboxydans* IFO 3254, *Gluconobacter suboxydans* IFO 3255, *Gluconobacter suboxydans* IFO 3256, *Gluconobacter suboxydans* IFO 3257, *Gluconobacter suboxydans* IFO 3258, *Gluconobacter suboxydans* IFO 3289, *Gluconobacter suboxydans* IFO 3290, *Gluconobacter suboxydans* IFO 3291, *Acetobacter aceti subsp. aceti* IFO 3281, *Acetobacter aceti subsp. orleansis* IFO 3259, *Acetobacter aceti subsp. xylinum* IFO 3288, *Acetobacter aceti subsp. xylinum* IFO 13772 and *Acetobacter liquefaciens* IPO 12388.

These microorganisms, which can be employed in the process of the present invention, include those which are being preserved in a public depository (culture collection) for delivery to any one upon request such as the Institute of Fermentation Osaka, Japan (IFO). Of these, a specific and preferred microorganism, *Gluconobacter suboxydans* IFO 3255, has been deposited at the Deutsche Sammlung von Mikroorganismen und Zellkulturen GmbH (DSM), Mascheroder Weg 1b, D-38124 Braunschweig, Germany on Feb. 13, 1995 under the Budapest Treaty. The allotted deposit number is DSM 9715.

The microorganism may be cultured in an aqueous medium supplemented with appropriate nutrients under aerobic conditions. The cultivation may be conducted at a pH of 3.5 to 8.0, preferably 5.0 to 7.5. The cultivation period varies depending upon the microorganism and the nutrient medium to be used, and is preferably about 6 to 100 hours. A preferred temperature range for carrying out the cultivation is from about 20° C. to about 40° C., preferably from about 25° C. to about 35° C.

It is usually required that the culture medium contains such nutrients as: assimilable carbon sources, such as glycerol, D-mannitol, D-sorbitol, erythritol, ribitol, xylitol, arabitol, inositol, dulcitol, D-ribose, D-fructose, D-glucose and sucrose, preferably D-sorbitol, D-mannitol or glycerol; digestible nitrogen sources such as organic substances, for example, peptone, yeast extract, baker's yeast and corn steep liquor, and inorganic substances, for example, ammonium sulfate, ammonium chloride and potassium nitrite; vitamins; and trace elements.

In the following, an embodiment for isolation and purification of the SLDH from the microorganisms after the cultivation is briefly described.

(1) Cells are harvested from the liquid culture broth by centrifugation or filtration.

(2) The harvested cells are washed with water, physiological saline or a buffer solution having an appropriate pH.

(3) The washed cells are suspended in the buffer solution and disrupted by means of a homogenizer, sonicator, French press or treatment with lysozyme and the like to give a solution of disrupted cells.

(4) The SLDH is isolated and purified from the cell free extract of disrupted cells, preferably from the membrane fraction of the microorganism.

The SLDH provided by the present invention is useful as a catalyst for the production of L-sorbose from D-sorbitol. The reaction should be conducted at pH values of about 5.5 to about 8.0, preferably from 6.0 to 7.0, in the presence of an electron acceptor, for example, DCIP, PMS, ferricyanide, cytochrome c and the like in a solvent such as phosphate buffer, tris buffer, citrate buffer and the like. A preferred temperature range for carrying out the reaction is from about 20° C. to about 50° C., preferably from 20° C. to 40° C. When the pH and temperature are set at about 6.5 to 7.5 and 30° C., respectively, the reaction usually gives particularly good results. Depending upon other reaction conditions such as the amount of enzyme, D-sorbitol, electon acceptor, pH, temperature or aeration speed, the D-sorbitol is completely converted to L-sorbose within about 2 to 24 hours, preferably within about 12 hours. The concentration of D-sorbitol in a solvent varies depending upon other reaction conditions, but in general is suitably from about 10 to about 300 g/L, most preferably from about 10 to about 200 g/L.

In addition to the above, the cultured cells are also useful for the production of ketoses from polyols, especially for the production of L-sorbose from D-sorbitol. L-Sorbose produced from D-sorbitol in a solvent is isolated by a combination of such conventional methods as centrifugation and concentration. However, the solvent containing L-sorbose without the isolation step can also be used as the starting material in the industrial production of vitamin C by the Reichstein method.

In the reaction, the enzyme may also be used in an immobilized state with an appropriate carrier. Any means of immobilizing an enzyme generally known in the art may be used. For instance, the enzyme may be bound directly to a membrane, granules or the like of a resin having functional group(s), or it may be bound to the resin through bridging compounds having bifunctional group(s), for example, glutaraldehyde.

The following Examples illustrate the present invention.

EXAMPLE 1

Preparation of D-sorbitol dehydrogenase (1) Cultivation of *Gluconobacter suboxydans* IFO 3255

*Gluconobacter suboxydans* IFO 3255 (DSM 9715) was supplied by the Institute for Fermentation, Osaka (IFO), and used throughout this study. The medium consisted of 20 g of D-sorbitol, 3 g of yeast extract, 3 g of beef extract, 3 g of corn steep liquor, 10 g of polypeptone, 1 g of urea, 1 g of $KH_2PO_4$, 0.2 g of $MgSO_4 \cdot 7H_2O$, and 1 g of $CaCO_3$ in 1 liter of deionized water. The pH was adjusted at 7.0 with sodium hydroxide before the addition of $CaCO_3$. The cultivation in a flask was carried out aerobically with rotary shaking for one day, or that in a 30-liter jar fermentor was carried out for 21.5 hours at 30° C., 500 rpm for agitation and 15 L/min. for aeration. The broth was centrifuged at 400×g for 10 minutes to remove calcium carbonate, and then at 10,000×g to pellet the cells. The cell cake was washed once with physiological saline. Thus, the intact cells (200 g wet weight) were obtained from 20 liters of culture. The cells were frozen at −20° C. until used.

(2) Preparation of membrane fraction

The cells (100 g wet weight) were suspended in 200 ml of 50 mM phosphate buffer (pH 7.0) and passed through a French pressure cell press at 20,000 psi. After centrifugation to remove intact cells, the supernatant (cell free extract) was centrifuged at 80,000×g for one hour and this precipitate was designated as the membrane fraction (2.28 g wet weight).

(3) Solubilization

The SLDH was isolated from the membrane fraction of *Gluconobacter suboxydans* IFO 3255 (DSM 9715). At first, the method reported by E. Shinagawa, K. Matsushita, O. Adachi and M. Ameyama, (*Agric. Biol. Chem.*, 46, 135–141, 1982), was used to solubilize the SLDH. The solubilization was performed by treating the membrane with 0.01M sodium acetate buffer (pH 5.0) containing 1% Triton X-100, 0.1M KCl, 0.1M D-sorbitol and about 10 mg/ml of the membrane protein for 2 hours at 5° C. However, the SLDH activity was not recovered from the membrane fraction and the whole activities in both solubilized supernatant and residual membrane fraction were lost under the above conditions.

Therefore, the effects of the solubilization conditions such as pH value, the concentration of buffer, detergents and KCl on the SLDH activity were studied. The recovery of SLDH activity was 74% into solubilized supernatant from the membrane fraction, when the membrane fraction was mixed in 0.05M potassium phosphate buffer (pH 7.0) containing 1% Triton X-100 and 0.04M D-sorbitol for 2 hours at 5° C. as shown in Table 8. The enzyme was not solubilized with n-octyl-β-D-glucopyranoside and the activity was lost by the addition of 0.1M KCl.

TABLE 8

Solubilization of membrane-bound D-sorbitol dehydrogenase

| Reaction mixture for the solubilization | Relative activity of D-sorbitol dehydrogenase after solubilization (%) | |
|---|---|---|
| | in the supernatant solubilized | in the membrane remained |
| (1) Membrane fraction before solubilization | | 100 |
| (2) Solubilization in 0.01M sodium acetate buffer (pH 5.0) containing 0.1M KCl and 0.1M D-sorbitol. | | |
| with 0.5% Triton X-100 | 0 | 0 |
| 1.0% Triton X-100 | 0 | 0 |
| 0.2% n-octyl-β-glucopyranoside | 6 | 0 |
| 0.3% n-octyl-β-glucopyranoside | 8 | 0 |
| (3) Solubilization at various concentrations of potassium phosphate buffer (pH 7.0) containing 1% Triton X-100 without KCl. | | |
| 0.01M buffer + 0.04M D-sorbitol | 23 | 2.5 |
| 0.05M buffer + 0.04M D-sorbitol | 74 | 6 |
| 0.1M buffer + 0.04M D-sorbitol | 38.5 | 3.5 |
| 0.05M buffer without D-sorbitol | 65.5 | 5 |
| (4) Solubilization in 0.05M potassium phosphate buffer (pH 7.0) containing 0.04M D-sorbitol. with 0.5% n-octyl-β-glucopyranoside | 2 | 119 |

To give the active fraction of SLDH for the isolation step {Example 1–(4)} from the membrane fraction of *Gluconobacter suboxydans* IFO 3255 (DSM 9715), frozen membranes were thawed and suspended in the buffer (pH 7.0) to give about 10 mg/ml of protein, and then 1% Triton X-100 and 0.1M D-sorbitol were added. The suspension was shaken at 180 rpm for 2 hours, and then centrifuged at 80,000×g for 60 minutes to remove the precipitate. The SLDH activity was recovered in the solubilized supernatant (200 ml).

(4) Diethylaminoethyl (hereinafter referred to as DEAE) -cellulose column chromatography The solubilized supernatant (200 ml) obtained Example 1–(3) was put on a column of DEAE-cellulose (2.5×30 cm) equilibrated and washed with the buffer (pH 7.0) containing 0.05M D-sorbitol and 0.1% Triton X-100. Elution of the enzyme was performed with 0.1M NaCl in the same buffer. The fractions having enzyme activity were collected.

(5) DEAE-Sepharose column chromatography

The pooled enzyme fractions (125 ml) from the previous step were dialyzed against two batches of one liter of the buffer containing 0.05M D-sorbitol and 0.1% Triton X-100, and put on a DEAE-Sepharose column (1.5×50 cm) equilibrated and washed with the same buffer, and the SLDH activity was eluted with a linear gradient of NaCl (0 to 0.2M). Major enzyme activity was eluted at NaCl concentration ranging from 0.16 to 0.18M.

6) Hydroxylapatite column chromatography

The pooled active fraction (40 ml) from the previous step was dialyzed against two batches of 500 ml of the buffer containing 0.05M D-sorbitol and 0.1% Triton X-100. A part of the enzyme (5 ml) was put on a hydroxylapatite column (2.5×20 cm) equilibrated. The enzyme activity was eluted during the washing of the column. After the same preparation had been repeated, fractions having enzyme activity were collected. The total volume was 52 ml after the active fraction was dialyzed against the buffer. Then the fraction was concentrated to 10 ml by ultra-filtration (PM10, Amicon).

(7) Sephacryl HR300 column chromatography

A portion of the enzyme fraction (2 ml) from the previous step was put on a Sephacryl HR300 column (1×120 cm) equilibrated with the buffer (pH 7.0) containing 0.05M NaCl, 0.05M D-sorbitol and 0.1% Triton X-100 and developed. This fractionation step was repeated and the active fraction was combined. The active fraction dialyzed against the buffer (13 ml) was pooled and stored at −80° C.

Summary of the purification steps of the enzyme is shown in Table 9.

TABLE 9

Purification of membrane-bound D-sorbitol dehydrogenase from *Gluconobacter suboxydans* IFO3255 (DSM 9715)

| Step | Volume (ml) | Total activity (units) | Total protein (mg) | Specific activity (units/mg-protein) | Recovery (%) |
|---|---|---|---|---|---|
| Cell free extract | 320 | 9,939 | 9,024 | 1.10 | 100 |
| Membrane fraction | 100 | 6,894 | 2,280 | 3.02 | 69.4 |
| Solubilized fraction | 200 | 2,878 | 1,480 | 1.94 | 29.0 |
| DEAE-Cellulose (DE52) | 125 | 1,812 | 250 | 7.25 | 18.2 |
| DEAE-Sepharose (CL6B) | 40 | 924.0 | 56.5 | 16.4 | 9.29 |
| Hydroxylapatite (BIO-GEL HTP) | 52 | 415.4 | 13.46 | 30.9 | 4.18 |
| Sephacryl S300 | 13 | 173.5 | 3.83 | 45.3 | 1.75 |

(8) Purity of the isolated enzyme

The purified enzyme with a specific activity of 45.43 units per mg of protein (0.2 mg/ml) was used for the following analysis.

The molecular weight of the native D-sorbitol dehydrogenase was determined by HPLC (detection, 254 μm; flow rate, 1 ml/min) using a size exclusion gel column (TSK gel G3000 SWXL column, 7.8 by 300 mm) equilibrated with 0.1M potassium phosphate buffer (pH 7.0) containing 0.3M NaCl. The molecular weight standards cyanocobalamin (1.35K), myoglobin (17K), ovalbumin (44K), γ-globulin (158K) and thyroglobulin (670K) were used. The purified enzyme showed a single peak and the molecular weight was determined to be about 800,000±50,000.

In the presence of sodium dodecyl sulfate (SDS), the enzyme showed a single band with a molecular weight of about 79,000±5,000. From these results, the purified SLDH consisted of ten homologous subunits.

(9) Identification of the reaction product

To identify the product converted from each substance, the reaction mixture (1 ml) containing 0.04M each of D-sorbitol, D-mannitol, D-arabitol, erythritol, D-adonitol and glycerol, and 8 mM PMS was incubated for 4 hours at 30° C. in 0.2M potassium phosphate buffer (pH 7.0) with 2.0 units of the purified enzyme. The reaction product was analyzed by HPLC and thin layer chromatography. L-Sorbose, D-fructose, D-xylulose, erythrulose, D-ribulose and dihydroxyacetone were produced from D-sorbitol, D-mannitol, D-arabitol, erythritol, D-adonitol and glycerol, respectively.

EXAMPLE 2

L-Sorbose production by purified SLDH

A reaction mixture (total volume 1.04 ml) containing 0.2 ml of purified SLDH (0.04 mg protein), 0.04 ml of 0.2M PMS, 0.1 ml of 0.4M D-sorbitol, 0.4 ml of 0.5M potassium phosphate buffer (pH 7.0) and 0.3 ml of water was incubated at 30° C. with gentle shaking. As a result, L-sorbose was formed at the rate of about 1.3 mg/hour.

EXAMPLE 3

Distribution of membrane-bound D-sorbitol dehydrogenase

Distribution of membrane-bound D-sorbitol dehydrogenase in various acetic acid bacteria was surveyed by the immunological blotting assay using the antibody against the SLDH provided in the present invention. Each cell homogenate of various acetic acid bacteria was treated with SDS to put each 20 µl of the solution containing 3 to 5 µg of protein on SDS polyacrylamide gel, and then the electrophoresis was carried out. Protein bands developed in the gel were electrophoretically transferred to the nitrocellulose membrane and reacted with the antibody. Then the nitrocellulose membrane was treated by using the Bio-Rad Immun-Blot kit for Goat Anti-Rabbit, and it was investigated as to which microorganism showed the positive band at the position of molecular weight (MW) 79,000±1,000. As shown in Table 10, all of the tested Gluconobacter strains and *Acetobacter aceti* subsp. *orleansis* IFO 3259, *Acetobacter aceti* subsp. *xylinum* IFO 3288 and *Acetobacter aceti xylinum* IFO 13772 showed the positive band. The cell homogenate of *Acetobacter aceti* subsp. *aceti* IFO 3281 and *Acetobacter liquefaciens* IFO 12388 showed weakly positive band at the position of MW 79,000±1,000.

TABLE 10

| Immunoblotting analysis by using the antibody of SLDH | |
|---|---|
| Strain | Immunoblotting analysis |
| Gluconobacter albidus IFO 3250 | + |
| G. albidus IFO 3251 | + |
| G. albidus IFO 3253 | + |
| G. capsulatus IFO 3462 | + |
| G. cerinus IFO 3263 | + |
| G. cerinus IFO 3264 | + |
| G. cerinus IFO 3265 | + |
| G. cerinus IFO 3267 | + |
| G. cerinus IFO 3270 | + |
| G. dioxyacetonicus IFO 3271 | + |
| G. dioxyacetonicus IFO 3274 | + |
| G. gluconicus IFO 3171 | + |
| G. gluconicus IFO 3285 | + |
| G. gluconicus IFO 3286 | + |
| G. industrius IFO 3260 | + |
| G. melanogenus IFO 3292 | + |

TABLE 10-continued

| Immunoblotting analysis by using the antibody of SLDH | |
|---|---|
| Strain | Immunoblotting analysis |
| G. melanogenus IFO 3293 | + |
| G. melanogenus IFO 3294 | + |
| G. nonoxygluconicus IFO 3276 | + |
| G. oxydans IFO 3189 | + |
| G. oxydans subsp. sphaericus IFO 12467 | + |
| G. roseus IFO 3990 | + |
| G. rubiginosus IFO 3244 | + |
| G. suboxydans IFO 3130 | + |
| G. suboxydans IFO 3172 | + |
| G. suboxydans IFO 3254 | + |
| G. suboxydans IFO 3255 (DSM 9715) | + |
| G. suboxydans IFO 3256 | + |
| G. suboxydans IFO 3257 | + |
| G. suboxydans IFO 3258 | + |
| G. suboxydans IFO 3289 | + |
| G. suboxydans IFO 3290 | + |
| G. suboxydans IFO 3291 | + |
| Acetobacter aceti subsp. aceti IFO 3281 | weakly positive |
| A. aceti subsp. orleansis IFO 3259 | + |
| A. aceti subsp. xylinum IFO 3288 | + |
| A. aceti subsp. xylinum IFO 13772 | + |
| A. liquefaciens IFO 12388 | weakly positive |

+: The crossing band was strongly detected at the position of MW 79,000 ± 1,000.

We claim:

1. A homogenous D-sorbitol dehydrogenase enzyme from a microorganism of the genus Gluconobacter or Acetobacter which enzyme catalyzes the oxidation of D-sorbitol to L-sorbose and which is further characterized by:

a) a molecular weight of 800,000±50,000;

b) a structure consisting of ten homologous subunits having a molecular weight of 79,000±5,000, each;

c) the ability of the enzyme to oxidize D-sorbitol to L-sorbose at a pH in the range of pH 5.5 to 8.0; and d) an optimum pH at which the enzyme oxidizes D-sorbitol to L-sorbose which is in the range from pH 6.0 to 7.0.

2. The D-Sorbitol dehydrogenase of claim 1 wherein the microorganism is selected from the group consisting of *Gluconobacter albidus* IFO 3250, *Gluconobacter albidus* IFO 3251, *Gluconobacter albidus* IFO 3253, *Gluconobacter capsulatus* IFO 3462, *Gluconobacter cerinus* IFO 3263, *Gluconobacter cerinus* IFO 3264, *Gluconobacter cerinus* IFO 3265, *Gluconobacter cerinus* IFO 3267, *Gluconobacter cerinus* IFO 3270, *Gluconobacter dioxyacetonicus* IFO 3271, *Gluconobacter dioxyacetonicus* IFO 3274, *Gluconobacter gluconicus* IFO 3171, *Gluconobacter gluconicus* IFO 3285, *Gluconobacter gluconicus* IFO 3286, *Gluconobacter industrius* IFO 3260, *Gluconobacter melanogenus* IFO 3292, *Gluconobacter melanogenus* IFO 3293, *Gluconobacter melanogenus* IFO 3294, *Gluconobacter nonoxygluconicus* IFO 3276, *Gluconobacter oxydans* IFO 3189, *Gluconobacter oxydans* subsp. *sphaericus* IFO 12467, *Gluconobacter roseus* IFO 3990, *Gluconobacter rubiginosus* IFO 3244, *Gluconobacter suboxydans* IFO 3130, *Gluconobacter suboxydans* IFO 3172, *Gluconobacter suboxydans* IFO 3254, *Gluconobacter suboxydans* IFO 3255 (DSM 9715), *Gluconobacter suboxydans* IFO 3256, *Gluconobacter suboxydans* IFO 3257, *Gluconobacter suboxydans* IFO 3258, *Gluconobacter suboxydans* IFO 3289, *Gluconobacter suboxydans* IFO 3290, *Gluconobacter suboxydans* IFO 3291, *Acetobacter aceti* subsp. *aceti* IFO 3281, *Acetobacter aceti* subsp. *orleansis* IFO 3259, *Acetobacter aceti* subsp. *xylinum* IFO 3288, *Acetobacter aceti* subsp. *xylinum* IFO 13772 and *Acetobacter liquefaciens* IFO 12388.

3. The D-Sorbitol dehydrogenase of claim 2 wherein the micoorganism is *Gluconobacter suboxydans* IFO 3255 (DSM 9715).

4. A process for producing L-sorbose from D-sorbitol which comprises reacting the D-sorbitol in an aqueous medium under aerobic conditions in the presence of:

1) a catalytically effective amount of a D-sorbitol dehydrogenase enzyme from a microorganism of the genus Gluconobacter or Acetobacter which enzyme catalyzes the oxidation of D-sorbitol to L-sorbose and which is further characterized by:
   a) a molecular weight of 800.000±50.000;
   b) a structure consisting of ten homologous subunits having a molecular weight of 79.000±5.000, each;
   c) the ability of the enzyme to oxidize D-sorbitol to L-sorbose at a pH in the range of pH 5.5 to 8.0; and
   d) an optimum pH at which the enzyme oxidizes D-sorbitol to L-sorbose which is in the range from pH 6.0 to 7.0;

and, 2) an electron acceptor in an amount effective to allow oxidation of D-sorbitol to L-sorbose;

whereby the D-sorbitol is oxidized to the L-sorbose.

5. The process of claim 4 wherein the electron acceptor is selected from the group consisting of 2,6-dichlorophenolindophenol, phenazine methosulfate, ferricyanide and cytochrome c.

6. The process of claim 5 wherein the reaction is carried out at a pH in the range from about 5.5 to about 8.0 and at a temperature in the range from about 20° to about 50° C.

7. The process of claim 6 wherein the reaction is carried out at a pH in the range from about 6.0 to 7.0 and at a temperature in the range from about 20° to 40° C.

8. The process of claim 5 wherein the microorganism is selected from the group consisting of *Gluconobacter albidus* IFO 3250, *Gluconobacter albidus* IFO 3251, *Gluconobacter albidus* IFO 3253, *Gluconobacter capsulatus* IFO 3462, *Gluconobacter cerinus* IFO 3263, *Gluconobacter cerinus* IFO 3264, *Gluconobacter cerinus* IFO 3265, *Gluconobacter cerinus* IFO 3267, *Gluconobacter cerinus* IFO 3270, *Gluconobacter dioxyacetonicus* IFO 3271, *Gluconobacter dioxyacetonicus* IFO 3274, *Gluconobacter gluconicus* IFO 3171, *Gluconobacter gluconicus* IFO 3285, *Gluconobacter gluconicus* IFO 3286, *Gluconobacter industrius* IFO 3260, *Gluconobacter melanogenus* IFO 3292, *Gluconobacter melanogenus* IFO 3293, *Gluconobacter melanogenus* IFO 3294, *Gluconobacter nonoxygluconicus* IFO 3276, *Gluconobacter oxydans* IFO 3189, *Gluconobacter oxydans* subsp. *sphaericus* IFO 12467, *Gluconobacter roseus* IFO 3990, *Gluconobacter rubiginosus* IFO 3244, *Gluconobacter suboxydans* IFO 3130, *Gluconobacter suboxydans* IFO 3172, *Gluconobacter suboxydans* IFO 3254, *Gluconobacter suboxydans* IFO 3255 (DSM 9715), *Gluconobacter suboxydans* IFO 3256, *Gluconobacter suboxydans* IFO 3257, *Gluconobacter suboxydans* IFO 3258, *Gluconobacter suboxydans* IFO 3289, *Gluconobacter suboxydans* IFO 3290, *Gluconobacter suboxydans* IFO 3291, *Acetobacter aceti* subsp. *aceti* IFO 3281, *Acetobacter aceti* subsp. *orleansis* IFO 3259, *Acetobacter aceti* subsp. *xylinum* IFO 3288, *Acetobacter aceti* subsp. *xylinum* IFO 13772 and *Acetobacter liquefaciens* IFO 12388.

9. The process of claim 8 wherein the micoorganism is *Gluconobacter suboxydans* IFO 3255 (DSM 9715).

10. The process of claim 9 wherein the reaction is carried out at a pH in the range from about 5.5 to about 8.0 and at a temperature in the range from about 20° to about 50° C.

11. The process of claim 10 wherein the reaction is carried out at a pH in the range from about 6.0 to 7.0 and at a temperature in the range from about 20° to 40° C.

* * * * *